United States Patent
Wagner et al.

(10) Patent No.: US 7,517,474 B2
(45) Date of Patent: Apr. 14, 2009

(54) CARBAMATE-FUNCTIONAL TRIAZINE DERIVATIVES

(75) Inventors: Eva Wagner, Speyer (DE); Reinhold Schwalm, Wachenheim (DE); Joerg Schneider, Wezembeek-Oppern (BE); Rainer Erhardt, Mannheim (DE); Carl Jokisch, Heidelberg (DE); Heinz-Peter Rink, Muenster (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 223 days.

(21) Appl. No.: 11/547,476

(22) PCT Filed: Apr. 8, 2005

(86) PCT No.: PCT/EP2005/003688

§ 371 (c)(1),
(2), (4) Date: Oct. 5, 2006

(87) PCT Pub. No.: WO2005/100326

PCT Pub. Date: Oct. 27, 2005

(65) Prior Publication Data

US 2007/0209553 A1   Sep. 13, 2007

(30) Foreign Application Priority Data

Apr. 14, 2004   (DE) .................. 10 2004 018 543

(51) Int. Cl.
*C07D 251/54*   (2006.01)
*C07D 251/70*   (2006.01)
*C09D 175/04*   (2006.01)

(52) U.S. Cl. .............. 252/401; 252/405; 544/196; 544/197

(58) Field of Classification Search .............. 544/196, 544/197; 252/401
See application file for complete search history.

(56) References Cited

U.S. PATENT DOCUMENTS 4,939,213 A   7/1990   Jacobs, III et al.

FOREIGN PATENT DOCUMENTS

| DE | 102 57 094 | 6/2004 |
|----|-----------|--------|
| EP | 0 604 922 | 7/1994 |
| EP | 0 622 387 | 11/1994 |
| WO | 87 00851  | 2/1987 |

*Primary Examiner*—Venkataraman Balasubramanian
(74) *Attorney, Agent, or Firm*—Oblon, Spivak, McClelland, Maier & Neustadt, P.C.

(57) ABSTRACT

New triazine derivatives containing carbamate groups, processes for preparing them, and their use.

22 Claims, No Drawings

CARBAMATE-FUNCTIONAL TRIAZINE DERIVATIVES

The present invention relates to new carbamate-functional triazine derivatives, to processes for preparing them, and to their use.

The German patent application with the file reference DE 102 57 094.9 describes an enzymatically catalyzed process for preparing carbamate-functional (meth)acrylic esters.

Triazines as a substructure are not described therein.

WO 87/00851 discloses coating compositions comprising mixtures of compounds having a carbamate structure and a crosslinking organic polymer containing a multiplicity of reactive hydroxyl groups and/or carbamate groups, such as, for example, amino resins and methylolated amino resins and diisocyanates or blocked diisocyanates.

Polyfunctional carbamates are not described; nor are carbamates attached to melamines.

It was an object of the present invention to provide new crosslinkers for film-forming binders, giving binders having improved properties.

This object has been achieved by means of carbamate-functional 1,3,5-triazine derivatives (F) of formula (I)

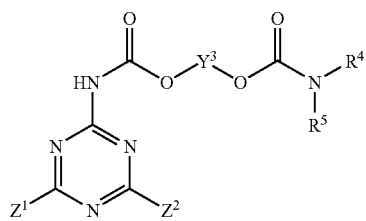

in which $Z^1$ is —NH$_2$, —NH—COOR$^1$, —NH—COO—Y$^1$—O—CO—NR$^6$R$^7$ or —NCO, $Z^2$ is —NH$_2$, —NH—COOR$^2$, —NH—COO—Y$^2$—O—CO—NR$^8$R$^9$ or —NCO, $Y^1$, $Y^2$ and $Y^3$ independently of one another are $C_2$—$C_{20}$ alkylene, $C_5$—$C_{12}$ cycloalkylene or are $C_2$—$C_{20}$ alkylene which is interrupted by one or more oxygen and/or sulfur atoms and/or by one or more substituted or unsubstituted imino groups and/or by one or more cycloalkyl, —(CO)—, —O(CO)O—, —(NH)(CO)O—, —O(CO)(NH)—, —O(CO)— or —(CO)O groups, it being possible for the stated radicals to be substituted in each case by aryl, alkyl, aryloxy, alkyloxy, heteroatoms and/or heterocycles, $R^4$, $R^5$, $R^6$, $R^7$, $R^8$ and $R^9$ independently of one another are hydrogen, $C_1$—$C_{18}$ alkyl which is uninterrupted or interrupted by one or more oxygen and/or sulfur atoms and/or by one or more substituted or unsubstituted imino groups, or are $C_2$—$C_{18}$ alkyl, $C_2$—$C_{18}$ alkenyl, $C_6$—$C_{12}$ aryl, $C_5$—$C_{12}$ cycloalkyl or a five- or six-membered heterocycle containing oxygen, nitrogen and/or sulfur atoms, it being possible for the stated radicals to be substituted in each case by aryl, alkyl, aryloxy, alkyloxy, heteroatoms and/or heterocycles, and $R^4$ and $R^5$, or $R^6$ and $R^7$, or $R^8$ and $R^9$ can also together form a ring, or are a group of the formula —[X$_i$]$_k$—H, $R^1$ and $R^2$ independently of one another are $C_1$ to $C_4$ alkyl, k is a number from 1 to 50 and $X_i$ for each i=1 to k can be selected independently of the others from the group consisting of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin—O—, —CHVin—CH$_2$—O—, —CH$_2$—CHPh-O— and —CHPh—CH$_2$—O—, where Ph is phenyl and Vin is vinyl.

The present invention further provides a process for preparing 1,3,5-triazine derivatives (F) of formula (I) by c) reacting an alcohol (C) containing urethane groups with at least one 1,3,5-triazine carbamate (D) of formula (II)

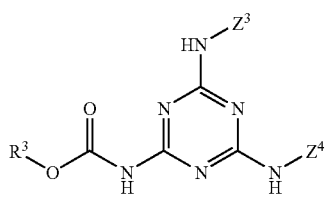

in which $Z^3$ is —NH$_2$ or —NH—COOR$^1$, $Z^4$ is —NH$_2$ or —NH—COOR$^2$, $R^1$ and $R^2$ are as defined above, and $R^3$ is $C_1$ to $C_4$ alkyl, followed by d) purification, if appropriate, of the reaction mixture from c).

The present invention additionally provides a process for preparing compounds F of formula (I) which contain isocyanate groups and in which at least one of the groups $Z^1$ and $Z^2$ is an isocyanate group (—NCO) by reacting an alcohol (C) containing urethane groups with 2,4,6-triisocyanato-1,3,5-triazine.

Urethane groups for the purposes of this specification are O-substituted and N-unsubstituted, monosubstituted or disubstituted structural units of the formula >N—C(=O)—O—.

Alcohols (C) containing urethane groups are compounds which contain at least one urethane group, preferably 1 to 10, more preferably 1 to 5, very preferably 1 or 2 and in particular one urethane group, and also at least one hydroxyl group (—OH), preferably 1 to 10, more preferably 1 to 6, very preferably 1 to 3, in particular 1 or 2, and especially one hydroxyl group.

Preferred alcohols (C) containing urethane groups have an average molar weight of 105 to 800,000 g/mol, preferably 120 to 25,000, more preferably 200 to 5000 and very preferably 400 to 4500 g/mol.

Particularly preferred alcohols (C) containing urethane groups are those obtainable by a) reacting an amine (A) with a carbonate (B) and b) purifying, if appropriate, the reaction mixture obtainable from a).

Amines in this context are ammonia, primary or secondary amines; carbonates are O,O'-disubstituted, cyclic or open-chain carbonates containing the structural unit —O—C(=O)—O—.

Especially preferred alcohols (C) containing urethane groups are those obtainable by reaction in accordance with formula (III)

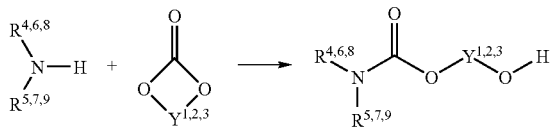

in which
$R^4, R^5, R^6, R^7, R^8, R^9, Y^1, Y^2$ and $Y^3$ are as defined above.

Preferably at least one of the two radicals $Z^1$ and $Z^2$ is selected from the group consisting of
$Z^1$—NH—COOR$^1$, —NH—COO—$Y^1$—O—CO—NR$^6$R$^7$ and —NCO, and
$Z^2$—NH—COOR$^2$, —NH—COO—$Y^2$—O—CO—NR$^8$R$^9$ and —NCO;

more preferably at least one of the two radicals $Z^1$ and $Z^2$ is selected from the group consisting of
$Z^1$—NH—COOR$^1$ and —NH—COO—$Y^1$—O—CO—NR$^6$R$^7$, and
$Z^2$—NH—COOR$^2$ and —NH—COO—$Y^2$—O—CO—NR$^8$R$^9$;

very preferably at least one of the two radicals $Z^1$ and $Z^2$ is
$Z^1$—NH—COO—$Y^1$—O—CO—NR$^6$R$^7$, or
$Z^2$—NH—COO—$Y^2$—O—CO—NR$^8$R$^9$;

and in particular both radicals are
$Z^1$—NH—COO—$Y^1$—O—CO—NR$^6$R$^7$ and
$Z^2$—NH—COO—$Y^2$—O—CO—NR$^8$R$^9$.

Preferably $R^4, R^5, R^6, R^7, R^8$ and $R^9$ independently of one another are hydrogen, $C_1$—$C_{12}$ alkyl, $C_5$—$C_6$ cycloalkyl or a group of the formula —[$X_i$]$_k$—H; more preferably $R^4, R^5, R^6, R^7, R^8$ and $R^9$ independently of one another are hydrogen, $C_1$—$C_4$ alkyl, $C_5$—$C_6$ cycloalkyl or a group of the formula —[$X_i$]$_k$—H, and very preferably they are hydrogen, $C_1$—$C_4$ alkyl or a group of the formula —[$X_i$]$_k$—H. In particular one of the radicals $R^4$ and $R^5$ or $R^6$ and $R^7$ or $R^8$ and $R^9$ respectively is hydrogen and the other is $C_1$—$C_4$ alkyl or a group of the formula —[$X_i$]$_k$—H, and in particular they are in each case both hydrogen.

$Y^1, Y^2$ and $Y^3$, independently of one another, are preferably $C_2$-$C_{10}$ alkylene, more preferably $C_2$—$C_6$ alkylene, very preferably $C_2$—$C_4$ alkylene, in particular $C_2$—$C_3$ alkylene and especially $C_2$ alkylene, it being possible for the stated radicals to be substituted in each case by aryl, alkyl, aryloxy, alkyloxy, heteroatoms and/or heterocycles.

k is preferably 1 to 30, more preferably 1 to 20, very preferably 1 to 10, and in particular 1 to 5.

Preferred $X_i$ are —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O— and —CH(CH$_3$)—CH$_2$—O—, particular preference being given to —CH$_2$—CH$_2$—O—, —CH$_2$—CH$_2$—N(H)—, —CH$_2$—CH$_2$—CH$_2$—N(H)—, —CH$_2$—CH(CH$_3$)—O— and —CH(CH$_3$)—CH$_2$—O—, and very particular preference to —CH$_2$—CH$_2$—O—, —CH$_2$—CH(CH$_3$)—O— and —CH(CH$_3$)—CH$_2$—O—.

Examples of $R^4, R^5, R^6, R^7, R^3$ and/or $R^9$ are hydrogen, $C_1$ to $C_4$ alkyl, which in this specification means methyl, ethyl, iso-propyl, n-propyl, n-butyl, iso-butyl, sec-butyl or tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, 2-hydroxyethyl, 2-hydroxypropyl, 1-hydroxypropyl, 5-hydroxy-3-oxapentyl, 8-hydroxy-3,6-dioxaoctyl or 11-hydroxy-3,6,9-trioxaundecyl.

Examples of $Y^1, Y^2$ and/or $Y^3$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, or

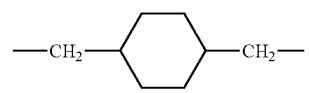

or 1,2-, 1,3- or 1,4-cyclohexylene, preference is given to 1,2-ethylene, 1,2-propylene, 1,3-propylene, particular preference to 1,2-ethylene and 1,2-propylene, and very particular preference to 1,2-ethylene.

$R^1, R^2$ and $R^3$ are in each case independently of one another methyl, ethyl, iso-propyl, n-propyl, n-butyl, iso-butyl, sec-butyl, tert-butyl; methyl, ethyl and n-butyl are preferred, methyl and n-butyl are especially preferred, and particular preference is given to methyl.

The radicals $R^1, R^2$ and $R^3$ can be identical or different; preferably they comprise not more than two different radicals. Exemplary amines (A) are ammonia, methylamine, dimethylamine, ethylamine, diethylamine, iso-propylamine, diiso-propylamine, n-butylamine, di-n-butylamine, tert-butylamine, monoethanolamine, diethanolamine, propanolamine, dipropanolamine, piperidine, piperazine, pyrrolidine, cyclopentylamine, cyclohexylamine, aniline, ethylene diamine, diethylenetriamine, triethylenetetramine, tetraethylenepentamine and polyethyleneimines having a weight-average molecular weight $M_w$ of 200 to 25,000 g/mol, preferably from 400 to 8,000, more preferably from 750 to 5000, and very preferably from 800 to 3,000 g/mol.

Further amines (A) may be for example hydrogenated polyacrylonitriles, straight-chain, branched or dendritic polymers containing amino functions, or at least partly hydrolyzed poly-N-vinylformamides.

Straight-chain polymers containing amino functions are for example polyethylene glycols, polypropylene glycols, mixed polyalkylene oxides, poly-1,3-propanediols, poly-THF or alkoxylated polyols or monools in which at least one terminal hydroxyl group has been replaced by an amino group, and also amino-functionalized polyisobutenes, in each case having a weight-average molecular weight $M_w$ of 200 to 25,000 g/mol, preferably 400 to 8,000, more preferably 750 to 5000, and very preferably 800 to 3,000 g/mol. Examples thereof are Jeffamines® from Huntsman Corp., Houston.

Branched polymers containing amino functions are described for example in WO 93/14147, p. 2, line 3-p. 6, line 14, the preparation thereof being described in the same specification and also in WO 95/02008 and WO 97/23514, or branched polymers of the kind whose preparation is described in WO 95/20619, and also the polyethylene glycol-polyethyleneimine block polymers described in Biomacromolecules, 2002, 3, 926-936.

Preferred branched polymers are for example the dendrimers obtainable starting from 1,4-diaminobutane, by alternating Michael addition of acrylonitrile and hydrogenation of the nitrile group, said dendrimers being of the 1st generation (Astramol® Am-4, from DSM, Netherlands, CAS No. [120239-63-6]), of the 2nd generation (Astramol@) Am-8, from DSM, Netherlands, CAS No. [154487-83-9]), of the 3rd generation (Astramol® Am-16, CAS No. [154487-85-1]), of the 4th generation (Astramol® Am-32, CAS No. [163611-04-9]) or of the 5th generation (Astramol® Am-64, CAS No. [163611-05-0]).

At least partly hydrolyzed poly-N-vinylformamides are described for example in EP B1 71 050, p. 1, line 31 to p. 4, line 54. Preference is given to hydrolyzed poly-N-vinylformamides having a K value (in accordance with Fikentscher, measured in 0.5% strength by weight aqueous sodium chloride solution at 25° C.) of between 10 and 110, particular preference being given to K values of between 30 and 80, and having a degree of cleavage (degree of hydrolysis of the formyl group) of 10 to 100 mol %, preferably 10 to 80, more preferably 20 to 60, and very preferably 30 to 50 mol %. Of these stated amines, preference is given to primary amines and ammonia, and particular preference to ammonia as amine.

Exemplary carbonates (B) are dimethyl carbonate, diethyl carbonate, di-n-propyl carbonate, diisopropyl carbonate, di-n-butyl carbonate, 1,2-ethylene carbonate, 1,3-propylene carbonate and 1,2-propylene carbonate, preference being given to dimethyl carbonate, di-n-butyl carbonate, 1,2-ethylene carbonate, 1,3-propylene carbonate and 1,2-propylene carbonate, and particular preference to 1,2-ethylene carbonate, 1,3-propylene carbonate and 1,2-propylene carbonate.

Reaction of an amine (A) with a carbonate (B) is conventional, being known for example from U.S. Pat. No. 4,820,830, col. 4, line 44 to col. 5, line 9, and is not subject to any restriction.

Typically the amine (A) and the carbonate (B) are reacted with one another in a stoichiometry of 0.7 to 1.2 mol of amine: 1 mol of carbonate, preferably 0.8-1.2:1, more preferably 0.9-1.1:1, very preferably 0.95-1.1:1, and in particular 1:1 mol/mol.

The reaction takes place in general at a temperature of 0 to 120° C., in particular at 20 to 100° C., very preferably 30 to 80° C., and with very particular preference 40 to 80° C.

The reaction is generally over within 12 hours, preferably within 15 minutes to 10 hours, more preferably in 30 minutes to 8 hours, very preferably 45 minutes to 6 hours, and in particular within from 1 to 4 hours.

The reaction can be carried out without solvent or in the presence of a solvent, examples being alcohols, ethers, ketones, hydrocarbons or water. It is preferably conducted without solvent.

The reaction mixture obtainable from a) can be purified if desired in a further step b), by means for example of filtration, distillation, rectification, chromatography, ion exchanger treatment, adsorbents, neutral, acidic and/or alkaline scrubbing, stripping or crystallization.

One preferred embodiment of the present invention provides carbamate-functional 1,3,5-triazine derivatives obtainable by a) reacting a primary amine or, more preferably, ammonia with a carbonate (B) at a temperature of 0 to 120° C., if appropriate under superatmospheric pressure,
b) purifying, if appropriate, the reaction mixture obtainable from a),
c) reacting the reaction mixture from a) or b) with at least one 1,3,5-triazine carbamate (D) or 2,4,6-triisocyanato-1,3,5-triazine and
d) purifying, if appropriate, the reaction mixture from c).

In step c) the reaction of the alcohol (C) containing urethane groups with at least one 1,3,5-triazine derivative (D) or 2,4,6-triisocyanato-1,3,5-triazine takes place if appropriate in the presence of a catalyst (E).

Particularly preferred compounds (C) are 2-hydroxyethyl carbamate (carbamic acid 2-hydroxyethyl ester), 2-hydroxypropyl carbamate, 2-hydroxy-1-methylethyl carbamate, and 3-hydroxypropyl carbamate.

Preferred 1,3,5-triazine carbamates (D) are the methyl-1,3,5-triazine carbamates, ethyl-1,3,5-triazine carbamates, n-butyl-1,3,5-triazine carbamates or mixed methyl/n-butyl-1,3,5-triazine carbamates.

The compounds (F) of formula (I) can be prepared by a purely thermal reaction or, preferably, by a catalyzed reaction, catalyzed with at least one catalyst (E) of compounds (D) with alcohols (C) containing urethane groups.

In the case of the thermal reaction regime the reaction is carried out at a temperature of up to 140° C., preferably up to 130° C.

Since the temperature in the catalyzed process is lower than in the case of the purely thermal preparation, in the former process it is generally possible to obtain more favorable color numbers.

The radicals $R^1$-$R^3$ in the compounds (D) of formula (III) are in each case independently of one another derived from alcohols $R^1OH$, $R^2OH$ and $R^3OH$ which have a boiling point under atmospheric pressure of 120° C. or less, preferably of 100° C. or less, more preferably of 80° C. or less and very preferably of 70° C. or less.

Particular preference in the process of the invention is given to those alcohols (C) containing urethane groups, of which the lowest-boiling alcohol (C) exhibits a boiling-point difference of at least 20° C., preferably at least 40° C. and more preferably at least 60° C. above the highest-boiling alcohol of the alcohols $R^1OH$, $R^2OH$ and $R^3OH$.

In the case of the catalyzed reaction regime the catalyst (E) in accordance with the invention is preferably selected from the group consisting of tin compounds, cesium salts, alkali metal carbonates and tertiary amines. Contemplation might additionally be made of using, as catalysts, alkoxides (examples being sodium or potassium alkoxides of $C_1$—$C_4$ alkyl alcohols, preferably sodium and potassium methoxide and ethoxide), hydroxides (NaOH, KOH, Ca(OH)$_2$, for example), carboxylates (sodium or potassium salts of $C_1$—$C_4$ alkylcarboxylic acids or ClCH$_2$COONa, for example), oxides (CaO, MgO, ZnO, Tl$_2$O$_3$, PbO, for example), phosphines (an example being PPh$_3$), zinc salts (ZnCl$_2$), and ion exchangers (strongly or weakly alkaline anion exchangers, such as DOWEX® MSA-1).

Tin compounds embrace all organometallic tin compounds, preferably tin(II) n-octanoate, tin(II) 2-ethylhexanoate, tin(II) laurate, dibutyltin oxide, dibutyltin dichloride, dibutyltin diacetate, dibutyltin dilaurate, dibutyltin dimaleate or dioctyltin diacetate, more preferably tin(II) n-octanoate, tin(II) 2-ethylhexanoate, tin(II) laurate, dibutyltin oxide, dibutyltin diacetate, dibutyltin dilaurate, very preferably dibutyltin oxide, dibutyltin diacetate, dibutyltin dilaurate, and in particular dibutyltin dilaurate.

Tin compounds, however, are toxicologically objectionable and therefore less preferred in accordance with the invention, especially when they remain in the reaction mixture. Contrastingly cesium salts and alkali metal carbonates are unobjectionable.

Preferred cesium salts are those containing the following anions: $F^-$, $Cl^-$, $ClO^-$, $ClO_3^-$, $ClO_4^-$, $Br^-$, $I^-$, $JO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, $(OC_mH_{2m+1})^-$, $(C_mH_{2m-1}O_2)^-$, $(C_mH_{2m-3}O_2)^-$, and $(C_{m+1}H_{2m-2}O_4)^{2-}$, where m stands for the numbers 1 to 20.

Particular preference is given to cesium carboxylates in which the anion conforms to formulae $(C_mH_{2m-1}O_2)^-$ and $(C_{m+1}H_{2m-2}O_4)^{2-}$ with m being from 1 to 20. Especially preferred cesium salts contain monocarboxylate anions of the general formula $(C_mH_{2m-1}O_2)^-$ where m stands for a number from 1 to 20. Particular mention may be made in this context of the formate, acetate, propionate, hexanoate, and 2-ethylhexanoate; very particular preference is given to cesium acetate.

The cesium salts can be added to the batch in solid form or in dissolved form. Suitable solvents include polar, aprotic solvents and protic solvents. Particular suitability is possessed, in addition to water, by alcohols; polyols are especially suitable, such as ethane-, propane- or butanediols and glycol ethers, for example.

In order to improve the solubility of the cesium salts in the reaction medium they can be used if appropriate with phase transfer catalysts. Examples of suitable phase transfer catalysts include crown ethers such as 18-crown-6 or tetraalkylammoinum salts such as tetrabutylammonium bromide. Alkali metal carbonates are for example $Li_2CO_3$, $Na_2CO_3$ and $K_2CO_3$ and also the hydrogencarbonates $LiHCO_3$, $NaHCO_3$ and $KHCO_3$, preference being given to $Na_2CO_3$ and $K_2CO_3$ and particular preference to $K_2CO_3$.

Tertiary amines are for example trioctylamine, tridodecylamine, tribenzylamine, N,N,N',N'-tetramethylethylenediamine, 1-methylpyrrole, pyridine, 4-dimethylaminopyridine, picoline, N,N'-dimethylpiperazine, N-methylmorpholine, N-methylpiperidine, N-ethylpiperidine, N,N-dimethylaniline, N,N-dimethylbenzylamine, N-methylimidazole, 1,4-diazabicyclo[2.2.2]octane, 1,5-diazabicyclo[4.3.0]non-5-ene or 1,8-diazabicyclo[5.4.0]undec-7-ene.

Preferred catalysts are cesium salts and alkali metal carbonates, particular preference being given to cesium salts.

The catalyst is employed normally in amounts of 0.001 to 0.3 mol %, preferably 0.005 to 0.25 mol %, more preferably 0.01 to 0.2 mol %, and very preferably 0.02 to 0.1 mol %, based on the starting compound (D).

The reaction is carried out in accordance with the invention at a temperature of at least 40° C., preferably at least 50° C., more preferably at least 60° C. and very preferably at least 70° C.

The reaction temperature is preferably above the boiling temperature of the alcohol $R^{10}H$, $R^2OH$ or $R^3OH$ that is to be separated off.

In the case of the purely thermal version the upper temperature limit is generally not more than 120° C., preferably not more than 110° C.

An advantage of the catalyzed reaction is that owing to the addition of the catalyst, for the same or a shorter reaction time and for at least equal conversion rates under otherwise identical conditions, can be lowered by at least 10° C., preferably at least 15° C. and more preferably at least 20° C. as compared with the uncatalyzed reaction.

The reaction time varies according to substrate and can be from 15 minutes to 12 hours, preferably 30 minutes to 10 hours, more preferably 45 minutes to 8 hours, and very preferably 1 to 7 hours.

The stoichiometry in terms of alcohol (C) employed in relation to carbamate groups that are to be converted in (D) is generally 0.5-1.5:1 mol/mol, preferably 0.7-1.3:1, more preferably 0.8:1.2:1, very preferably 0.8-1.1:1, in particular 0.9-1:1 and especially 0.95-1.0:1 mol/mol. Depending on the chosen stoichiometry between (C) and (D) the reaction mixture contains different fractions of 1,3,5-triazine derivatives of formula (I), in which preferably at least one of the groups $Z^1$ and $Z^2$ and more preferably both groups $Z^1$ and $Z^2$ is/are —NH—COO—$Y^1$—O—CO—$NR^6R^7$ or/and —NH—COO—$Y^2$—O—CO—$NR^8R^9$.

The reaction can take place in bulk or in a suitable solvent, i.e., a solvent which does not react with a 1,3,5-triazine carbamate or 2,4,6-triisocyanato-1,3,5-triazine. Examples of possible such alcohols include acetone, acetylacetone, ethyl acetoacetate, ethyl acetate, butyl acetate, ethylene glycol dimethyl ether, ethylene glycol diethyl ether, ethylene glycol di-n-butyl ether, diethylene glycol dimethyl ether, diethylene glycol diethyl ether, diethylene glycol di-n-butyl ether, $C_1$-$C_4$ alkylene carbonates, especially propylene carbonate, THF, dioxane, dimethylformamide, dimethyl sulfoxide, N-methylpyrrolidone, 1,3-dioxolane, iso-butyl methyl ketone, ethyl methyl ketone, diethyl ether, tert-butyl methyl ether, tert-butyl ethyl ether, n-pentane, n-hexane, n-heptane, cyclohexane, methylcyclohexane, benzene, toluene, xylene, paraffins, naphtha, mineral oil or petroleum ether fractions.

Preferably the reaction is carried out in bulk.

The conversion rates achieved with the stated process are generally at least 20%, preferably at least 30%, more preferably at least 40% and very preferably at least 60%.

The reaction can be carried out in a gas or gas mixtures which is insert under the reaction conditions, examples being those having an oxygen content of less than 10%, preferably less than 8% and more preferably less than 7% by volume, and preference being given to nitrogen, argon, helium, nitrogen/noble gas mixtures, carbon dioxide or carbon monooxide, and particular preference to nitrogen.

In one preferred embodiment of the process of the invention the liberated lower alcohols $R^1OH$, $R^2OH$ and $R^3OH$ are separated off appropriately, as a result of which the reaction equilibrium which is established is shifted in favor of the product.

The lower alcohol $R^1OH$, $R^2OH$ or $R^3OH$ can be separated off for example by distillation, stripping, reduced pressure, azeotropic removal, absorption, pervaporation, and diffusion via membranes.

Preference is given to distillative removal, under reduced pressure if appropriate, which if appropriate can be assisted by stripping with a gas which is inert under the reaction conditions.

For the purpose of stripping, a gas or gas mixture which is inert under the reaction conditions is passed through the reaction mixture, by being bubbled in, for example.

Absorption can take place for example with molecular sieves (with a pore size, for example, in the region of about 3-10 angstroms). Diffusion can take place for example with the aid of suitable semipermeable membranes.

The reaction can take place in accordance with the invention continuously, batchwise or semibatchwise, preference being given to batchwise or semibatchwise reactions.

For this purpose, in general, the starting material of formula (D) is introduced as an initial charge and is brought to the desired reaction temperature.

Before or after the desired reaction temperature has been reached, if desired, the catalyst (E), at least in part can be added and the alcohol (C) can be added in whole, in portions or continuously. If the catalyst has not yet been completely added, it too may be added subsequently in portions.

It can be advantageous to raise the reaction temperature in the course of the reaction, by at least 10° C. for example, preferably by at least 15° C. and more preferably by at least 20° C., as compared with the temperature at start of the reaction.

The course of the reaction can be monitored, for example, by monitoring the amount of alcohol $R^1OH$, $R^2OH$ and $R^3OH$ liberated and terminating the reaction at the desired conversion.

The reaction can be stopped, for example, by cooling the system down or by direct cooling with a solvent.

The reaction is preferably carried out in a reaction tank with backmixing, in which mixing may be effected, for example, by stirring, introduction through nozzles or by means of a pumped circulation.

Temperature adjustment may take place either by way of the reactor walls or by means of a heat exchanger which is located within the pumped circulation.

If the liberated lower alcohol $R^1OH$, $R^2OH$ or $R^3OH$ is separated off by distillation and/or stripping then a packed column or tray column can be mounted on the reactor, for which 2 to 10 theoretical plates are generally sufficient.

To assist with separation of the lower alcohol it is possible to apply a slight vacuum; for example, the reaction can be carried out at a pressure of from 200 hPa to atmospheric, preferably 300 hPa to atmospheric, more preferably 500 hPa to atmospheric, very preferably 800 hPa to atmospheric, and in particular at atmospheric pressure.

The end of the reaction may be followed by washing and/or decolorizing of the reaction mixture in step d).

For the purpose of washing, the reaction mixture is treated in a washer with a wash liquid, such as water or a 5-30%, preferably 5-20%, more preferably 5-15% strength by weight solution of sodium chloride, potassium chloride, ammonium chloride, sodium sulfate or ammonium sulfate, preferably water or sodium chloride solution.

Washing can be carried out, for example, in a stirred tank or in other conventional apparatus, such as in a column or mixer/settler apparatus.

If necessary the reaction mixture can be decolorized, by treatment for example with activated carbon or metal oxides, such as aluminum oxide, silicon oxide, magnesium oxide, zirconium oxide, boron oxide or mixtures thereof, in amounts of 0.1-50% by weight for example, preferably 0.5 to 25% by weight and more preferably 1-10% by weight, at temperatures of, for example, 10 to 100° C., preferably 20 to 80° C. and more preferably 30 to 60° C.

This operation can be performed by adding the powder or granules of decolorizer to the reaction mixture, followed by filtration, or by passing the reaction mixture over a bed of the decolorizer in the form of any desired suitable shapes.

In general the composition of the reaction mixture obtainable under the stated reaction conditions is as follows:

compounds of the formula (I) in which both groups $Z^1$ and $Z^2$ are —NH—COO—$Y^1$—O—CO—$NR^6R^7$ or —NH—COO—$Y^2$—O—CO—$NR^1R^9$: 5-80% by weight, compounds of the formula (I) in which one of the groups $Z^1$ and $Z^2$ is —NH—COO—$Y^1$—O—CO—$NR^6R^7$ or —NH—COO—$Y^2$—O—CO—$NR^8R^9$: 10-60% by weight, compounds of the formula (I) in which both groups $Z^1$ and $Z^2$ are not —NH—COO—$Y^1$—O—CO—$NR^6R^7$ or —NH—COO—$Y^2$—O—CO—$NR^8R^9$: 10-40% by weight, compounds of the formula (II): 0-20% by weight, alcohol (C) containing urethane groups: 0-10% by weight, if appropriate, traces of alcohols $R^1OH$, $R^2OH$ and $R^3OH$, and if appropriate, traces of the catalyst (E).

Furthermore, in those cases in which the radicals $R^4$ and/or $R^6$ and/or $R^8$ are hydrogen, it is also possible for the reaction to be accompanied by the formation, in minor amounts, of byproducts in which the alcohol of the formula (III) containing urethane groups is attached via the nitrogen atom located on the urethane group, so forming structures in which $Z^1$ is —NH—CO—$NR^7$—O—$Y^1$—OH and/or $Z^2$ is —NH—CO—$NR^9$—O—$Y^2$—OH and/or an analogous structure for the third urethane-group-containing alcohol —NH—CO—$NR^5$—O—$Y^3$—OH.

The preparation of compounds (I) in which at least one of the groups $Z^1$ and $Z^2$ is NCO from 2,4,6-triisocyanato-1,3,5-triazine may in principle take place in just the same way as described above, starting from the compound (D), but with the following differences:

The stoichiometry in respect of alcohol (C) employed in relationship to isocyanate groups to be converted in 2,4,6-triisocyanato-1,3,5-triazine is generally 0.5-1.2:1 mol/mol, preferably 0.7-1.1:1, more preferably 0.8:1.1:1, very preferably 0.9-1.1:1, in particular 0.9-1:1, and especially 0.95-1.0:1 mol/mol.

In general the reaction is carried out at temperatures between 5 and 100° C., preferably between 20 and 90° C. and more preferably between 40 and 80° C. and in particular between 60 and 80° C.

It is preferred in this case to operate under anhydrous conditions.

Anhydrous means that the water content of the reaction system is not more than 5%, preferably not more than 3% and more preferably not more than 1% by weight.

In order to accelerate the reaction of the diisocyanates it is possible to use the customary catalysts. Catalysts suitable for this purpose include in principle all those commonly used in polyurethane chemistry.

These are, for example, organic amines, especially tertiary aliphatic, cycloaliphatic or aromatic amines, and/or Lewis-acidic organometallic compounds. Examples of suitable Lewis-acidic organometallic compounds include the above-mentioned tin compounds, such as tin(II) salts of organic carboxylic acids, e.g., tin(II) acetate, tin(II) octoate, tin(II) ethylhexoate and tin(II) laurate, and the dialkyltin(IV) salts of organic carboxylic acids, e.g., dimethyltin diacetate, dibutyltin diacetate, dibutyltin dibutyrate, dibutyltin bis(2-ethylhexanoate), dibutyltin dilaurate, dibutyltin maleate, dioctyltin dilaurate and dioctyltin diacetate. Metal complexes as well are possible, such as acetylacetonates of iron, titanium, aluminum, zirconium, manganese, nickel and cobalt. Further metal catalysts are described by Blank et al. in Progress in Organic Coatings, 1999, Vol. 35, pages 19-29.

Preferred Lewis-acidic organometallic compounds are dimethyltin diacetate, dibutyltin dibutyrate, dibutyltin bis(2-ethylhexanoate), dibutyltin dilaurate, dioctyltin dilaurate, zirconium acetylacetonate and zirconium 2,2,6,6-tetramethyl-3,5-heptanedionate.

Bismuth and cobalt catalysts as well, and also cesium salts, can be employed as catalysts. Suitable cesium salts are the compounds mentioned above, preferably cesium acetate.

In view of the reactivity of the isocyanate groups in the compounds (I), washing is generally omitted.

If desired, however, it is possible to convert at least some of the isocyanate groups present in the reaction mixture into amino groups, such as by hydrolysis with water, or into urethane groups, such as by reaction with alcohols, or to carry out other isocyanate group transformations known from isocyanate group chemistry.

In general the composition of the reaction mixture obtainable under the stated reaction conditions is as follows:

compounds of formula (I) in which both groups $Z^1$ and $Z^2$ are NCO: 5-80% by weight, compounds of formula (I) in which one of the groups $Z^1$ and $Z^2$ is NCO: 10-60% by weight, compounds of the formula (I) in which both groups $Z^1$ and $Z^2$ are not NCO: 10-40% by weight, 2,4,6-triisocyanato-1,3,5-triazine: 0-20% by weight, alcohol (C) containing urethane groups: 0-10% by weight, and if appropriate, traces of the catalyst (E).

Here again the same byproducts may be present as described above.

After the end of the reaction the reaction mixture obtainable from c) can be used further without additional purification or if necessary it can be purified in a further step d).

d) The reaction mixture obtained from c) can be purified, as described above, by means of a filtration, distillation, rectification, chromatography, treatment with ion exchangers, adsorbents, neutral, acidic and/or alkaline washing, stripping or crystallization.

The 1,3,5-triazine derivatives obtainable from stages c) and/or d) can be used with advantage as comonomers in binders, preferably in dual-cure binders for coating compositions.

Coatings thus obtainable feature at least one of the following advantages, in comparison for example with conventional tris(alkoxycarbonylamino)triazines, melamine resins or carbamate-containing polyacrylates: very high scratch resistances, hardnesses, chemical and acid resistances, elasticity, good solubility and adhesion, on hydrophilic or even on hydrophobic substrates, low viscosity.

Coating compositions of this kind include, in addition to the triazine derivatives (F) of formula (I) of the invention, at least one compound containing at least one carbamate-reactive group.

Suitability for this purpose is possessed by those compounds which are able to crosslink with carbamates. Reactive groups of this kind include active methylol or alkylalkoxy groups, especially methylalkoxy groups, on amino resin crosslinkers, such as etherified reaction products of formaldehyde with amines, such as melamine, urea, etc., phenol/formaldehyde adducts, siloxane or silane groups, and anhydrides, as described for example in U.S. Pat. No. 5,770,650.

Among the technically widespread and known, preferred amino resins it is possible with particular preference to use urea resins and melamine resins, such as urea-formaldehyde resins, melamine-formaldehyde resins, melamine-phenol-formaldehyde resins or melamine-urea-form a dehyde resins, for example.

Suitable urea resins are those which are obtainable by reacting ureas with aldehydes and which can be modified if appropriate.

Suitable ureas are urea, N-substituted ureas or N,N'-disubstituted ureas, such as N-methylurea, N-phenylurea, N,N'-dimethylurea, hexamethylenediurea, N,N'-diphenylurea, 1,2-ethylenediurea, 1,3-propylenediurea, diethylenetriurea, dipropylenetriurea, 2-hydroxypropylenediurea, 2-imidazolidinone (ethyleneurea), 2-oxohexahydropyrimidine (propyleneurea) or 2-oxo-5-hydroxyhexahydropyrimidine (5-hydroxypropyleneurea).

Particularly suitable aldehydes are formaldehyde, acetaldehyde, iso-butyraldehyde and glyoxal.

Urea resins can if appropriate be partly or fully modified, by reaction for example with monofunctional or polyfunctional alcohols, ammonia and/or amines (cationically modified urea resins) or with (hydrogen)sulfites (anionically modified urea resins); particularly suitable resins in accordance with the invention are the alcohol-modified urea resins.

Suitable alcohols for the modification include $C_1$—$C_6$ alcohols, preferably $C_1$—$C_4$, and in particular methanol, ethanol, iso-propanol, n-propanol, n-butanol, iso-butanol and sec-butanol.

Suitable melamine resins are those which are obtainable by reacting melamine with aldehydes and which if appropriate may be partly or completely modified.

Melamine-formaldehyde resins are reaction products of melamine with aldehydes, such as the abovementioned aldehydes, formaldehyde in particular. If appropriate the resulting methylol groups are modified by etherification with the above-mentioned monohydric or polyhydric alcohols. It is also possible for the melamine-formaldehyde resins to be modified as described above by reaction with amines, aminocarboxylic acids or sulfites.

The action of formaldehyde on mixtures of melamine and urea or on mixtures of melamine and phenol produces melamine-urea-formaldehyde resins or melamine-phenol-formaldehyde resins, respectively, which are likewise possible for use in accordance with the invention.

The stated amino resins are prepared by methods which are known per se.

Particularly mentioned examples are melamine-formaldehyde resins, including monomeric or polymeric melamine resins and partly or fully alkylated melamine resins, urea resins, e.g., methylolurea resins such as formaldehyde-urea resins, alkoxyureas such as butylated formaldehyde-urea resins, but also N-methylolacrylamide emulsions, iso-butoxymethylacrylamide emulsions, polyanhydrides, such as polysuccinic anhydride, and siloxanes or silanes, e.g., dimethyldimethoxysilanes.

Particular preference is given to amino resins such as melamine-formaldehyde resins or formaldehyde-urea resins.

Also preferred are amino resins in which one or more amino groups have been substituted by carbamate groups, as described in U.S. Pat. No. 5,300,328.

The coating compositions may further comprise typical coatings additives, examples being antioxidants, stabilizers, activators (accelerators), fillers, pigments, dyes, antistats, flame retardants, thickeners, thixotropic agents, surface-active agents, viscosity modifiers, plasticizers or complexing agents.

As accelerators for the thermal aftercure it is possible, for example, to use tin octoate, zinc octoate, dibutyltin laurate or diazabicyclo[2.2.2]octane.

Additionally it is possible to add one or more initiators which can be activated photochemically and/or thermally, examples being potassium peroxodisulfate, dibenzoyl peroxide, cyclohexanone peroxide, di-tert-butyl peroxide, azobisisobutyronitrile, cyclo-hexylsulfonyl acetyl peroxide, diisopropyl percarbonate, tert-butyl peroctoate or benz-pinacol, and also, for example, those thermally activable initiators which have a half-life at 80° C. of more than 100 hours, such as di-t-butyl peroxide, cumene hydroperoxide, dicumyl peroxide, t-butyl perbenzoate, silylated pinacols, which are available commercially for example under the trade name ADDID 600 from Wacker, or hydroxyl-containing amine N-oxides, such as 2,2,6,6-tetramethylpiperidin-N-oxyl, 4-hydroxy-2,2,6,6-tetramethylpiperidin-N-oxyl, etc.

Further examples of suitable initiators are described in "Polymer Handbook", 2nd ed., Wiley & Sons, New York.

Suitable thickeners, besides free-radically (co)polymerized (co)polymers, include customary organic and inorganic thickeners such as hydroxymethylcellulose or bentonite.

As complexing agents it is possible for example to use ethylenediamineacetic acid and salts thereof and also β-diketones.

Suitable fillers include silicates, examples being silicates obtainable by hydrolyzing silicon tetrachloride, such as Aerosil® from Degussa, silicious earth, talc, aluminum silicates, magnesium silicates, calcium carbonates, etc.

Suitable stabilizers include typical UV absorbers such as oxanilides, triazines and benzotriazole (the latter available as Tinuvin® grades from Ciba-Spezialitätenchemie) and benzophenones. They can be used alone or together with suitable free-radical scavengers, examples being sterically hindered amines such as 2,2,6,6-tetramethylpiperidine, 2,6-di-tert-butylpiperidine or derivatives thereof, e.g. bis-(2,2,6,6-tetramethyl-4-piperidyl)sebacate. Stabilizers are used normally in amounts of 0.1 to 5.0% by weight, based on the solid components present in the formulation.

The substrates are coated by standard methods known to the skilled worker, involving application of at least one coating composition of the invention to the target substrate in the desired thickness and removal of the volatile constituents of the coating composition, with heating if appropriate. This operation can be repeated one or more times if desired. Application to the substrate may take place in a known way, as for example by spraying, trowelling, knife coating, brushing, rolling, roller coating or flow coating. The coating thickness is generally in a range from approximately 3 to 1000 g/m² and preferably 10 to 200 g/m².

The coating thus applied may be cured such that following application of the coating composition of the invention or of coating formulations a thermal treatment takes place at temperatures of up to 200° C., preferably up to 180° C., more preferably up to 160° C., very preferably between 60 and 160° C., and in particular between 60 and 150° C. As well as in coating compositions the compounds of the invention may also find application in microcapsules, including hollow microcapsules, for producing pigment preparations, and in the coating of films.

The examples which follow are intended to illustrate the properties of the invention, though not restricting it.

EXAMPLES

Parts are to be understood in this specification, unless indicated otherwise, as referring to parts by weight.

Example 1

A 500 ml four-necked glass flask with metal stirrer, thermocouple, distillation bridge and Dimroth condenser was charged with 75 g of a mixed methyl/n-butyl 1,3,5-triazine carbamate (0.2 mol), 21 g of 2-hydroxyethyl carbamate (0.2 mol) and 96 g of butyl acetate.

Using an oilbath the mixture was then heated to 90° C., forming a clear, pale yellowish solution. Subsequently 3 drops of dibutyltin dilaurate were added for catalysis and a mixture of methanol, butanol and butyl acetate was distilled off under a gentle stream of nitrogen for 16 hours.

The product was then transferred to a 500 ml Büchi beaker flask and solvent was distilled off on a rotary evaporator at 100° C. under a pressure <1 hPa.

Cooling gave a clear yellowish solid. H-NMR showed no remaining traces of free 2-hydroxyethyl carbamate. A statistical distribution of the possible condensation products was found.

Example 2

A 500 ml four-necked glass flask with metal stirrer, thermocouple, distillation bridge and Dimroth condenser was charged with 75 g of a mixed methyl/n-butyl 1,3,5-triazine carbamate (0.2 mol), 23.8 g of 2-hydroxypropyl carbamate (isomer mixture) (0.2 mol) and 98.8 g of butyl acetate.

Using an oilbath the mixture was then heated to 90° C., forming a clear, pale yellowish solution. Subsequently 3 drops of dibutyltin dilaurate were added for catalysis and a mixture of methanol, butanol and butyl acetate was distilled off under a gentle stream of nitrogen for 16 hours.

The product was then transferred to a 500 ml Büchi beaker flask and solvent was distilled off on a rotary evaporator at 100° C. under a pressure <1 hPa.

Cooling gave a clear yellowish solid. H-NMR showed no remaining traces of free 2-hydroxypropyl carbamate. A statistical distribution of the possible condensation products was found.

What is claimed is:

1. A 1,3,5-triazine compound represented by formula (I):

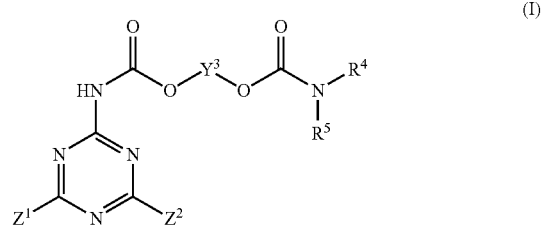

wherein $Z^1$ is —$NH_2$, —NH—COO$R^1$, —NH—COO—$Y^1$—O—CO—N$R^6R^7$ or —NCO, $Z^2$ is —$NH_2$, —NH—COO$R^2$, NH—COO—$Y^2$—O—CO—N$R^8R^9$ or —NCO, $Y^1$, $Y^2$ and $Y^3$, independently of one another, are $C_2$—$C_{20}$ alkylene, $C_5$—$C_{12}$ cycloalkylene or are $C_2$—$C_{20}$ alkylene which is interrupted by one or more oxygen and/or sulfur atoms and/or by one or more substituted or unsubstituted imino groups and/or by one or more cycloalkyl, (CO)—, —O(CO)O—, —(NH)(CO)O—, —O(CO)(NH)—, —O(CO)— or —(CO)O groups, wherein the $C_2$—$C_{20}$ alkylene, $C_5$—$C_{12}$ cycloalkylene or are $C_2$—$C_{20}$ alkylene may substituted by aryl, alkyl, aryloxy, alkyloxy, heteroatoms and/or heterocycles, $R^4$, $R^5$, $R^6$, $R^7$, $R^8$ and $R^9$, independently of one another, are hydrogen, $C_1$—$C_{18}$ alkyl, $C_2$—$C_{18}$ alkyl which is uninterrupted or interrupted by one or more oxygen and/or sulfur atoms and/or by one or more substituted or unsubstituted imino groups, or are $C_2$—$C_{18}$ alkenyl, $C_6$—$C_{12}$ aryl, $C_5$—$C_{12}$ cycloalkyl or a five- or six-membered heterocycle containing oxygen, nitrogen and/or sulfur atoms, wherein the $C_1$—$C_{18}$ alkyl, $C_2$—$C_{18}$ alkyl, $C_2$—$C_{18}$ alkenyl, $C_6$—$C_{12}$ aryl, $C_5$—$C_{12}$ cycloalkyl or a five- or six-membered heterocycle may be substituted by aryl, alkyl, aryloxy, alkyloxy, heteroatoms and/or heterocycles, or $R^4$ and $R^5$, or $R^6$ and $R^7$, or $R^8$ and $R^9$ can also together form a ring, or are a group of the formula —[$X_i$]$_k$—H, $R^1$ and $R^2$, independently of one another, are $C_1$ to $C_4$ alkyl, k is a number from 1 to 50, and $X_i$ for each i =1 to k is selected independently from the group consisting of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —CH$_2$—CH$_2$—CH$_2$—O—, —CH$_2$—CH$_2$—CH$_2$—CH$_2$—O—, —CH$_2$—CHVin—O—, —CHVin—CH$_2$—O—, —CH$_2$—CHPh—O— and —CHPh—CH$_2$—O—, where Ph is phenyl and Vin is vinyl.

2. The compound of claim 1, wherein Y$^1$, y$^2$ and/or Y$^3$ are selected from the group consisting of 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene,

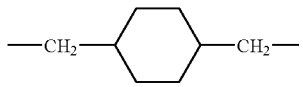

or 1,2-,1,3- or 1,4-cyclohexylene, and 2,2-dimethyl-1,4-butylene.

3. The compound of claim 2, wherein y$^1$, Y$^2$ and/or Y$^3$ are selected from the group consisting of 1,2-ethylene, 1,2-propylene and 1,3-propylene.

4. The compound of claim 1, wherein at least one of R$^4$ and R$^5$ or R$^6$ and R$^7$ or R$^8$ and R$^9$ is hydrogen.

5. The compound of claim 1, wherein at least one of Z$^1$ and Z$^2$ is selected from the group consisting of
Z$^1$—NH—COOR$^1$, —NH—COO—Y$^1$—O—CO—NR$^6$R$^7$ and —NCO, and
Z$^1$—NH—COOR$^2$, —NH—COO—Y$^2$—O—CO—NR$^8$R$^9$ and —NCO.

6. The compound of claim 1, wherein R$^4$ and R$^5$ or R$^6$ and R$^7$ or R$^8$ and R$^9$ are hydrogen.

7. The compound of claim 1, wherein Y$^1$, Y$^2$ and Y$^3$, independently of one another, are C$_2$—C$_{20}$ alkylene, C$_5$—C$_{12}$ cycloalkylene or are C$_2$—C$_{20}$ alkylene which is interrupted by one or more oxygen and/or sulfur atoms and/or by one or more substituted or unsubstituted imino groups and/or by one or more cycloalkyl, (CO)—, —O(CO)O—, —(NH)(CO)O—, —O(CO)(NH)—, —O(CO)— or —(CO)O groups, wherein the C$_2$-C$_{20}$ alkylene, C$_5$—C$_{12}$ cycloalkylene or are C$_2$—C$_{20}$ alkylene are substituted by aryl, alkyl, aryloxy, alkyloxy, heteroatoms and/or heterocycles.

8. The compound of claim 1, wherein Y$^1$, Y$^2$ and Y$^3$, independently of one another, are C$_2$—C$_{20}$ alkylene, C$_5$—C$_{12}$ cycloalkylene or are C$_2$—C$_{20}$ alkylene which is interrupted by one or more oxygen and/or sulfur atoms and/or by one or more substituted or unsubstituted imino groups and/or by one or more cycloalkyl, (CO)—, —O(CO)O—, —(NH)(CO)O—, —O(CO)(NH)—, —O(CO)— or —(CO)O groups.

9. The compound of claim 1, wherein R$^4$, R$^5$, R$^6$, R$^7$, R$^8$ and R$^9$, independently of one another, are hydrogen, C$_1$—C$_{18}$ alkyl, C$_2$—C$_{18}$ alkyl which is uninterrupted or interrupted by one or more oxygen and/or sulfur atoms and/or by one or more substituted or unsubstituted imino groups, or are C$_2$—C$_{18}$ alkenyl, C$_6$ C$_{12}$ aryl, C$_5$—C$_{12}$ cycloalkyl or a five- or six-membered heterocycle containing oxygen, nitrogen and/or sulfur atoms, wherein the C$_1$—C$_{18}$ alkyl, C$_2$—C$_{18}$ alkyl, C$_2$—C$_{18}$ alkenyl, C$_6$—C$_{12}$ aryl, C$_5$—C$_{12}$ cycloalkyl or a five- or six-membered heterocycle are substituted by aryl, alkyl, aryloxy, alkyloxy, heteroatoms and/or heterocycles.

10. The compound of claim 1, wherein R$^4$, R$^5$, R$^6$, R$^7$, R$^8$ and R$^9$, independently of one another, are hydrogen, C$_1$—C$_{18}$ alkyl, C$_2$—C$_{18}$ alkyl which is uninterrupted or interrupted by one or more oxygen and/or sulfur atoms and/or by one or more substituted or unsubstituted imino groups, or are C$_2$—C$_{18}$ alkenyl, C$_6$—C$_{12}$ aryl, C$_5$—C$_{12}$ cycloalkyl or a five- or six-membered heterocycle containing oxygen, nitrogen and/or sulfur atoms.

11. The compound of claim 1, wherein k is 1 to 20.

12. The compound of claim 1, wherein k is 1 to 10.

13. The compound of claim 1, wherein k is 1 to 5.

14. A process for preparing a 1,3,5-triazine compound of claim 1, comprising reacting an alcohol represented by the formula (R$^{4,6,8}$)(R$^{5,7,9}$)N—C(O)O—Y$^{1,2,3}$—OH with at least one 1,3,5-triazine represented by formula (II)

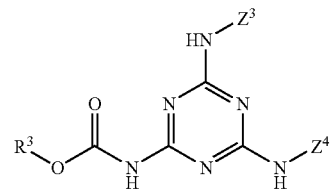

(II)

wherein
Z$^3$ is —NH$_2$ or —NH—COOR$^1$,
Z$^4$ is —NH$_2$ or —NH—COOR$^2$,
R$^1$, R$^2$, R$^4$, R$^5$, R$^6$, R$^7$, R$^8$, R$^9$, Y1, Y$^2$ and Y$^3$ are as defined above, and
R$^3$ is C$_1$ to C$_4$ alkyl.

15. The process of claim 14, further comprising purifying the 1,3,5-triazine compound.

16. The process of claim 14, comprising reacting the alcohol with 2,4,6-triisocyanato-1,3,5-triazine.

17. The process of claim 14, wherein at least one of the radicals R$^4$ and R$^5$ or R$^6$ and R$^7$ or R$^8$ and R$^9$ is hydrogen.

18. The process of claim 14, wherein at least one of Z$^1$ and Z$^2$ is selected from the group consisting of
Z$^1$—NH—COOR$^1$, —NH—COO—Y$^1$—O—CO—NR$^6$R$^7$ and —NCO and
Z$^2$—NH—COOR$^2$, —NH—COO—Y$^2$—O—CO—NR$^8$R$^9$ and —NCO.

19. The process of claim 14, wherein R$^4$ and R$^5$ or R$^6$ and R$^7$ or R$^8$ and R$^9$ are hydrogen.

20. A coating composition comprising
at least one triazine compound as defined in claim 1 and
at least one compound containing at least one carbamate-reactive group.

21. A method of making the composition of claim 20, comprising combining the at least one triazine compound and the at least one compound containing at least one carbamate-reactive group.

22. A method of incorporating a binder into a coating composition, comprising incorporating at least one triazine compound as defined in claim 1 into a coating composition.

* * * * *